United States Patent [19]

Lavoisier

[11] Patent Number: 5,692,520
[45] Date of Patent: Dec. 2, 1997

[54] METHOD AND APPARATUS FOR MEASURING ARTERIAL AND VENOUS BLOOD FLOW IN BODY APPENDAGES

[75] Inventor: Pierre Lavoisier, Lyons, France

[73] Assignee: Laborie Medical Technologies, Inc., Mississauga, Canada

[21] Appl. No.: 646,639

[22] Filed: May 8, 1996

[51] Int. Cl.$^6$ .................................................. A61B 5/010
[52] U.S. Cl. .................. 128/774; 128/667; 128/694; 128/748; 128/688
[58] Field of Search .................. 128/633, 664–7, 128/668, 670, 672, 677, 678, 687, 688, 691, 694, 748, 774

[56] References Cited

U.S. PATENT DOCUMENTS

| | | | |
|---|---|---|---|
| 4,747,415 | 5/1988 | Lavoisier | 128/774 |
| 4,848,361 | 7/1989 | Penney et al. | 128/774 |
| 4,913,162 | 4/1990 | Leang et al. | 128/774 |
| 4,928,706 | 5/1990 | Trick | 128/774 |
| 5,140,990 | 8/1992 | Jones et al. | 128/672 |
| 5,277,187 | 1/1994 | Pillsbury | 128/677 |
| 5,301,675 | 4/1994 | Tomita | 128/677 |
| 5,482,039 | 1/1996 | Place | 128/774 |
| 5,490,506 | 2/1996 | Takatani et al. | 128/666 |
| 5,568,814 | 10/1996 | Gallant et al. | 128/672 |

*Primary Examiner*—Jennifer Bahr
*Assistant Examiner*—Bryan K. Yarnell
*Attorney, Agent, or Firm*—Sherman and Shalloway

[57] ABSTRACT

The present invention is directed to a non-invasive method and apparatus for measuring arterial and venous blood flow in body appendages. The present invention is also directed to a non-invasive method and apparatus for measuring penile tumescence as a function of arterial and venous blood flow in the penis and penile rigidity as a function of suprasystolic intra-cavernosal pressure. These measurements are performed to make a diagnosis in the field of erectile dysfunctions. Since every normal adult male experiences erections during rapid eye movement sleep, the measurements are preferably made during the patient's sleep, but can also be performed when the patient is awake for diagnosis and treatment.

15 Claims, 3 Drawing Sheets

METHOD AND APPARATUS FOR MEASURING ARTERIAL AND VENOUS BLOOD FLOW IN BODY APPENDAGES

FIELD OF THE INVENTION

The present invention is directed to a non-invasive method and apparatus for measuring arterial and venous blood flow in body appendages. The present invention is also directed to a non-invasive method and apparatus for measuring penile tumescence as a function of arterial and venous blood flow in the penis and penile rigidity as a function of suprasystolic intra-cavernosal pressure. These measurements are performed to make a diagnosis in the field of erectile dysfunctions. Since every normal adult male experiences erections during rapid eye movement sleep, the measurements are preferably made during the patient's sleep, but can also be performed when the patient is awake for diagnosis and treatment.

BACKGROUND OF THE INVENTION

Measurement of nocturnal penile tumescence, hereinafter referred to as NPT, has been widely used to establish a differential diagnosis between organic impotence and psychogenic impotence. Patients with organic impotence will have no erections either when awake or during rapid eye movement sleep, while psychogenic patients will experience erections during sleep but not while awake.

Measurement of NPT is usually performed with the help of a plethysmograph. This device comprises a loop-shaped silicone elastomer tubing filled with mercury. The tubing is positioned around the penis of the patient and is connected to an electrical circuit. Any change in the circumference of the penis causes stretching of the silicone tubing which in turn triggers a variation in the electrical resistance of the mercury filling. The electrical circuit will measure this change in resistance which can then be translated into a measure of the increase in penile circumference. This measurement allows one to determine penile tumescence.

However, while the plethysmograph enables the measurement of penile tumescence, it does not provide a measure of penile rigidity which is important in determining whether vaginal penetration is possible. Penile rigidity is a function of the pressure inside the corpus cavernosum. Measurement of this pressure is sufficient to determine whether vaginal penetration is possible.

U.S. Pat. No. 4,747,415 describes a device for measuring intra-cavernosal pressure, hereinafter referred to as ICP. This device comprises a cuff including a non elastic band having one of its faces entirely covered with a plastic container filled with a liquid. The non elastic band is wrapped around the penis of the patient with the liquid container in direct contact with the penis. A pressure transducer is mounted in direct communication with the liquid inside the plastic container for sensing the pressure of the liquid. An electronic device is provided for amplifying the pressure signal given by the transducer and for recording and displaying this pressure. In use, any erection of the penis causes an increase in ICP which in turn compresses the liquid inside the container held in position by the non expandable cuff. The pressure recorded is perfectly correlated with the ICP.

During an erection, the corpus cavernosum fills up with blood. In the first phase, its volume will increase until it reaches its maximum. This is known as tumescence, characterized by subsystolic pressure. In the second phase, known as rigidity, ICP will rise to suprasystolic pressure levels. The corpus cavernosum comprises an arterial inflow and a venous outflow. For ICP to rise, it is necessary to have an increase in inflow simultaneously with a decrease in outflow.

When measurement of the ICP of the patient reveals an organic impotence, it remains to determine whether this is due to the absence of increase in inflow (arterial pathology) or absence of decrease in outflow (venous leak). Knowledge of the inflow, for example, would allow one to determine the origin of the organic impotence.

SUMMARY OF THE INVENTION

It is an object of the present invention to provide an apparatus and method for non invasive measurement of arterial and venous blood flow.

It is a further object of the present invention to provide a non invasive method and apparatus for measuring both ICP and changes in arterial and venous flows of the corpus cavernosum in order to distinguish between organic and psychogenic impotence and to determine, in the case of organic impotence, whether this is due to an arterial pathology or a venous leak.

Further objects and advantages of the present invention will become evident from the following drawings and description.

To this effect, the present invention provides an apparatus for measuring arterial and venous blood flow. The apparatus comprises:

a cuff including a flexible, non elastic band, one face of which is covered with at least one plastic container capable of being filled with a fluid, means to position, close and firmly hold the non elastic band around a body appendage of the patient, such as the penis, so that, in the closed position, the container will remain on the inside of the cuff, a pressure transducer in direct communication with the fluid inside the container to measure its pressure, and electronic means to modify the sensitivity of the pressure transducer and to amplify and/or display the signals generated by the transducer.

The apparatus further comprises a photoplethysmograph having a probe attachable to the container so that the light beam emitted by the probe is directable either toward the container and the fluid therein or toward the appendage around which the cuff is positioned. Also included are electronic means to modify the sensitivity of the photoplethysmograph and to amplify and/or display the signals generated thereby.

The method of this invention for measuring penile rigidity of the patient comprises the following steps:

prior to use, filling the at least one plastic container covering the internal face of the cuff with a fluid, liquid or gas, attaching the photoplethysmography probe to the outside of the container on the face opposite the non elastic band, positioning the cuff around the non erect penis of the patient with the fluid filled plastic container and the photoplethysmography probe in direct contact with the penis, measuring the fluid pressure inside the plastic container, during pressure measurement, activating the photoplethysmography probe to emit a light beam and measuring the reflected light using the photoelectric cell of the same probe, amplifying, recording and/or displaying the measurements performed.

The invention also provides a method of obtaining a curve of arterial blood flow changes which comprises the following steps:

recording the pulse signal generated by the photoplethysmography probe during the flaccid stage and then during tumescence for measured pressures inferior to a preset value, recording the pulse signal generated by the pressure transducer for pressures greater than the previous preset value, evaluating the pulse using the surface area under the curve obtained from the two previous recordings in order to obtain a curve of arterial blood flow changes.

The present invention further provides a method for obtaining the curve of venous blood flow changes whereby the presence of a venous leak may be determined. The method of obtaining this curve comprises the following steps:

obtaining the curve of arterial blood flow changes as described above, recording the pressure transducer signal for pressures below the preset pressure value, calculating from the previous pressure curve and the curve of arterial blood flow changes, using fluid mechanics laws, the changes in venous blood flow in order to obtain their curve.

If the arterial inflow increases without an increase in pressure and volume, it can be deduced that the inflow is equal to the outflow which allows one to establish that there is no blood retention in the penis.

Preferably, the method includes the continuous measurement of pulse frequency, duration and amplitude of ICP changes, as well as the measurement of arterial blood flow changes. It is then possible, from these measurements, to classify each patient in a group. To provide this classification, the following steps are added to the method:

measurement of fluid pressure according to the described method, plotting of the obtained curve, identification for each tumescence period of a pressure plateau corresponding to the vascular phase and of pressure peaks corresponding to the muscular phase, evaluation of the surface area of the plateau and the surface area of the peaks corresponding to the plateau, transfer of these results into a diagram with the plateau surface area on the X-axis and the surface area of the peaks on the Y-axis, or inversely, plotting of a curve with time on the X-axis and plateau pressure as well as maximum peak pressures on the Y-axis.

DETAILED DESCRIPTION OF THE INVENTION

Several embodiments of the apparatus are proposed. In a first embodiment, shown in FIG. 1, the cuff comprises one plastic container which is preferably filled with water. The use of water or another liquid is optimal for pressure measurement. In a second embodiment, shown in FIG. 2, the cuff comprises two containers, one filled with water in direct communication with the pressure transducer, the other filled with air and maintained at constant pressure and to the outside of which the photoplethysmography probe is attached on the face opposite the non elastic band. Although water and air are the preferred fluids for use in the apparatus, other fluids suitable for pressure measurement may be used.

The invention will be well understood by following the description below with reference to the drawings shown herein. These drawings are non restrictive examples of apparatus which conforms to the invention and provide means for implementation of the methods described herein.

Figure 1:
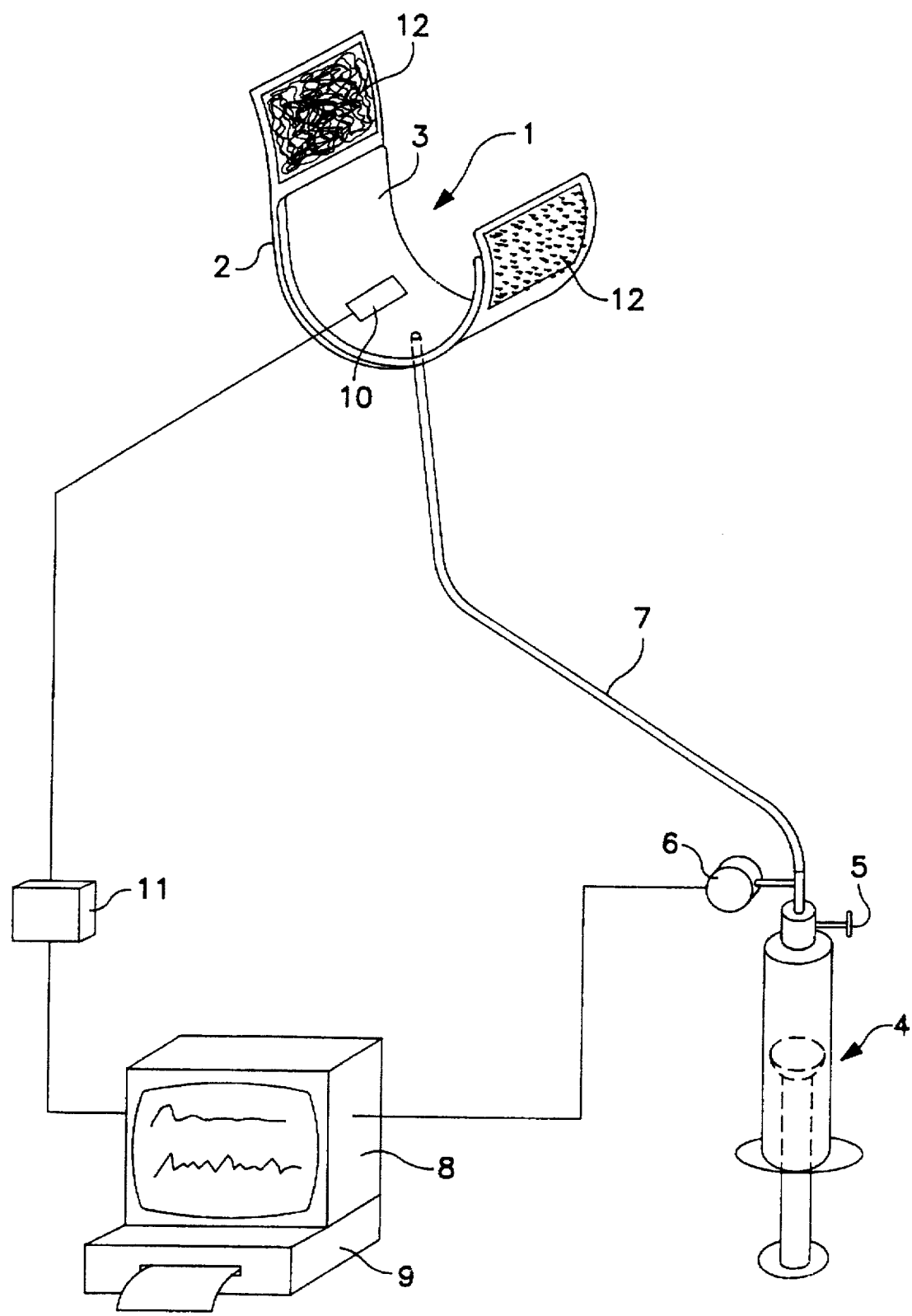
FIG. 1 is a schematic view of a first embodiment of the apparatus of the invention.

The first embodiment, an apparatus to measure ICP and blood flow in the penis of a patient, is represented in FIG. 1. The apparatus comprises a penile cuff 1 including a non elastic band 2 with one of its faces covered with a transparent plastic container 3 capable of being filled with a fluid, such as water, using a syringe 4. A stopcock 5 is mounted between the syringe 4 and the container 3 in order to be able to remove the syringe 4 once the container 3 is filled. A pressure transducer 6 measures the pressure inside the container 3. A pressure tubing line 7 links the pressure transducer 6 to the container 3.

The signals measured by the pressure transducer 6 are amplified and transmitted to a computer 8 which records them and displays them on its screen. The computer 8 also allows for numerical treatment of these signals in order to analyze them and produce a statistical analysis. A printer 9 allows printing of the curves displayed on the screen as well as of all numerical results.

The probe 10 of a photoplethysmograph 11 is attached to the outside of the container 3 on the face opposite the band 2. The probe 10 comprises a photo-emitting diode and a photoelectric cell. A light beam is emitted by the diode and the reflected beam is captured by the photoelectric cell. The probe 10 is preferably mounted so that the emitted light beam will be directed toward the skin of the appendage on which the cuff 1 is positioned. However, in some cases better measurements are obtained when the probe 10 is mounted so that the light beam is directed toward the cuff 1. Accordingly, it is considered to be within the scope of this invention to mount the probe 10 in either fashion.

The signal generated by the photoelectric cell is amplified, recorded into the memory of the computer 8 and can then be displayed on the computer screen and/or printed on the printer 9.

Every erection of the penis is the consequence of an increase in ICP and, with the plastic container being firmly held around the penis, this increase in pressure compresses the fluid inside the container. Therefore, the measurement of the pressure of the fluid allows one to know the ICP which is directly related to the rigidity of the penis.

The photoplethysmograph is used to measure blood flow. Such devices have been widely used to measure blood flow in capillaries under the skin. However, the most interesting blood flow to measure here is arterial flow inside the corpus cavernosum. The latter is surrounded by a thick membrane, the tunica albuginea, which can hardly be crossed by the light of a photoplethysmograph. Some measurements have revealed that the photoplethysmograph can measure penile blood flow when the light beam of the photoplethysmography probe is directed toward the skin. Surprisingly, measurements have also been found possible when the light beam of the photoplethysmography probe is directed toward the liquid filled container. In some instances these measurements are better than those obtained when the light is directed toward the skin. In this manner, a measurement of the global penile pulse and, therefore, of the global arterial flow of the penis, is obtained.

To carry out measurements of penile rigidity, the plastic container 3 is filled with water and the cuff 1 is then wrapped around the penis of the patient (not shown), while non erect, so that the plastic container 3 and the photoplethysmography probe are in direct contact with the penis.

When erection occurs, pressure inside the corpus cavernosum increases the container 3 is held between the penis, which exerts a pressure, and the non elastic band 2. The pressure inside the corpus cavernosum is transmitted to the container 3 which is compressed. During a predetermined period, a complete sleep period for example, the pressure transducer 6 measures pressure changes which are amplified and sent to the computer 8 for analysis.

Alternatively, the measurements taken by the pressure transducer 6 and the photoplethysmograph 11 may be stored by a portable recording unit 14 for later downloading to the computer 8. In this manner, the apparatus may be made portable and the patient may use the system at home to record nocturnal measurements and return the recording unit 14 to his doctor for subsequent downloading and analysis. In a further alternative, using common modem technology, the data may even be stored in the recording unit 14 and then transferred Via modem to the doctor's office.

Simultaneously, the photoplethysmograph 11 measures changes in arterial blood flow.

In the preferred manner of use, i.e., with the light emitted toward the skin, the photoplethysmograph provides a signal resulting from two physical phenomena:

absorption of emitted photons, mainly by red blood corpuscles, which absorption varies with the level of oxygenation of the red blood corpuscles, which changes during the erection, and reflection of the emitted photons by the walls of the vessels and tissues.

The light beam of a photoplethysmograph ordinarily has a low intensity and can only penetrate through a few millimeters of tissue. Therefore, it cannot ordinarily reach the internal face of the tunica albuginea and measure the blood flow in the cavernous artery within the tunica albuginea.

Surprisingly, it has also been noticed that by directing the light beam externally, i.e., toward the container 3 and the penile cuff 1, the photoplethysmograph 11 generates a signal which is synchronous with the penile pulse.

Variations of the signals generated by the photoplethysmograph are most likely linked to changes in the thickness of the container. These changes in thickness are more obvious at the beginning of the erection when ICP is low and the penis is still soft and therefore compressible.

After an increase in pressure in the corpus cavernosum, tissues are no longer compressible and changes in pulse amplitude cannot be transmitted to them anymore. Thus, the photoplethysmography probe 10 no longer records any variation. On the other hand, the pressure transducer continues to record the pressure changes.

Thus, the invention provides a means to obtain the curve of changes in penile arterial blood flow, in particular during an erection. This curve can be obtained from two sources:

the photoplethysmograph 11 during tumescence while ICP is low and inferior to a preset pressure, and the pressure transducer 6 which records the pulse on top of the pressure. These two curves are analyzed and the evaluation of the surface area under the curves obtained provides a means to calculate the arterial blood flow curve.

From this curve, it is also possible to get the curve of changes in venous blood flow. It is then necessary to measure ICP even for pressures inferior to the preset pressure value. Using the two curves obtained, ICP and changes in arterial pressure, and classical laws of fluid mechanics, changes in venous flow may be calculated and their curve plotted.

Knowledge of changes in venous blood flow provides information which can be directly exploited to assess venous leaks. Using this method it is also possible to identify pressure plateaus corresponding to tumescence and pressure peaks linked to contraction of the ischiocavernosus muscles.

Using computer systems with analysis of the signal, it is then possible to measure the surface area of the plateaus, the surface area of the peaks, the height of the peaks, the difference between the highest and the lowest pressure for each peak, the average of these differences, etc. From these measurements, a statistical analysis (factor analysis) identifies the two most representative parameters: the surface area of the peaks and the surface area of the plateaus.

In order to classify patients into groups to help the physician in his diagnosis, signals from the pressure transducer are recorded for a complete night during the patient's sleep. The corresponding curve is plotted. As previously indicated, to each tumescence period correspond a pressure plateau and one or more pressure peaks, the surface areas of which may be calculated. Results of these evaluations are then plotted on a chart with the surface area of peaks on the X-axis and the surface area of the plateau on the Y-axis. A curve with time on the X-axis and pressure on the Y-axis is also plotted and provides a representation of the pressure, the length of the pressure plateau and the maximum pressure of the peaks.

Four patient groups or clusters are identified:

1. weak: for whom the two surface areas measured are relatively small; they do not have tumescence, 2. average: with limited tumescence and erection lacking in rigidity, 3. muscular pathology: with satisfactory tumescence but little rigidity, 4. hyper: with satisfactory tumescence and rigidity.

The fact that the photoplethysmography signal drops when the ICP increases is a handicap that can be corrected by software. Establishing the relation between ICP and changes in the photoplethysmography signal is sufficient to obtain a measurement of the real flow.

In order to prevent these problems, it is preferable to have the photoplethysmography probe attached to a compressible container filled with air, which is compressible. Such a device (cuff 1 with a container 3 filled with air) also provides a means to measure pressure. However, to measure pressure it is preferable to use a non compressible fluid, such as water.

Figure 2:
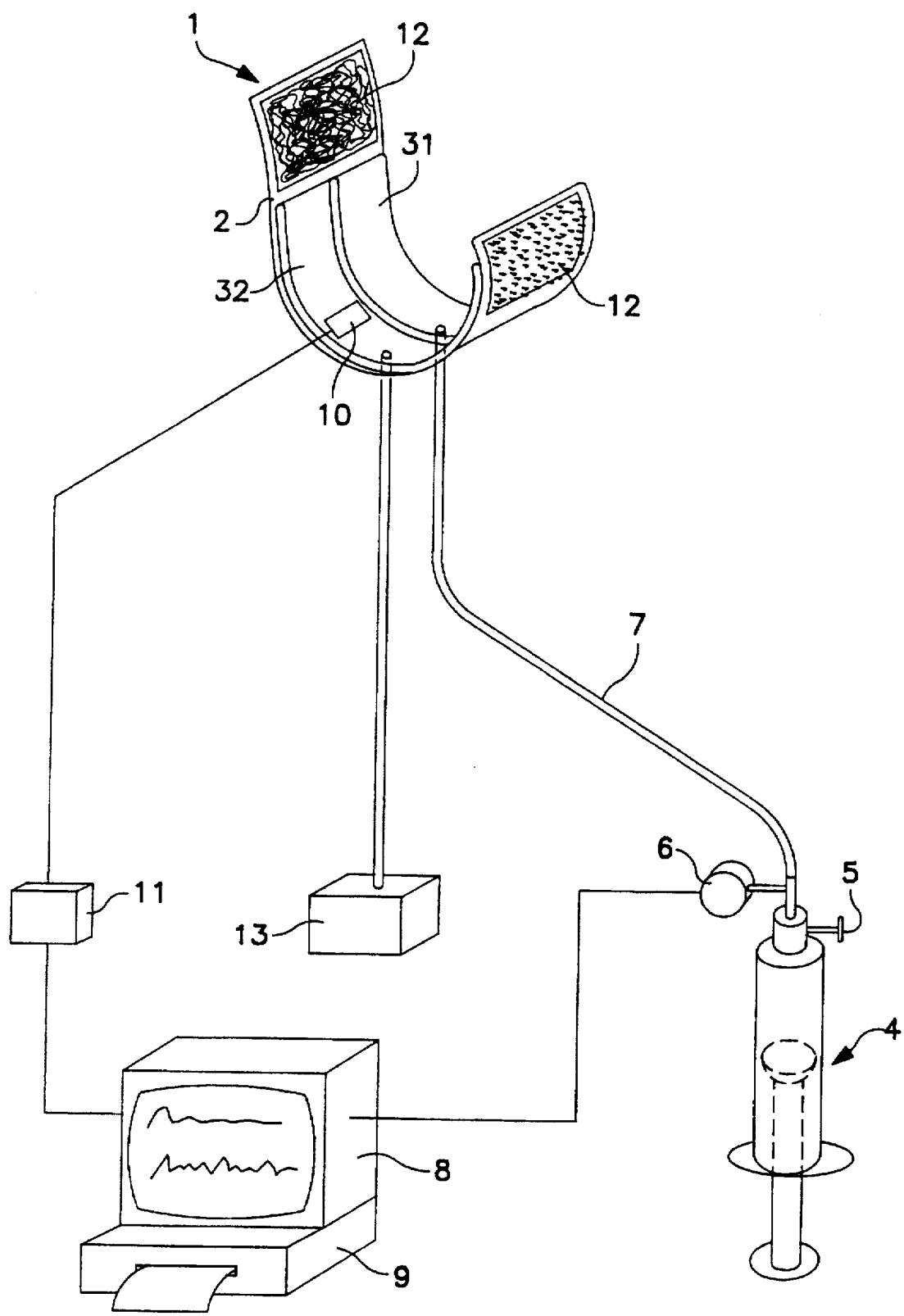
FIG. 2 is a schematic view of a second embodiment of the apparatus of the invention.

In an alternative embodiment of the apparatus represented in FIG. 2, the cuff 1 is provided with two containers 31 and 32. The first container 31 is filled with water and is used to measure pressure in the manner previously described for the apparatus of FIG. 1. The second container 32 is filled with air which is kept at a constant pressure using a pressure regulator 13. the photoplethysmography probe 10 is attached to the second container 32 which is transparent. As in the first embodiment, the light beam emitted by the photoplethysmography probe diode may be directed toward the container 32 or toward the skin of the appendage on which the cuff is positioned.

Measurements with this embodiment of the apparatus are carried out using the same method as with the first embodiment, the difference in this case being that the signal from the photoplethysmograph is more sensitive and more accurate.

Figure 3:
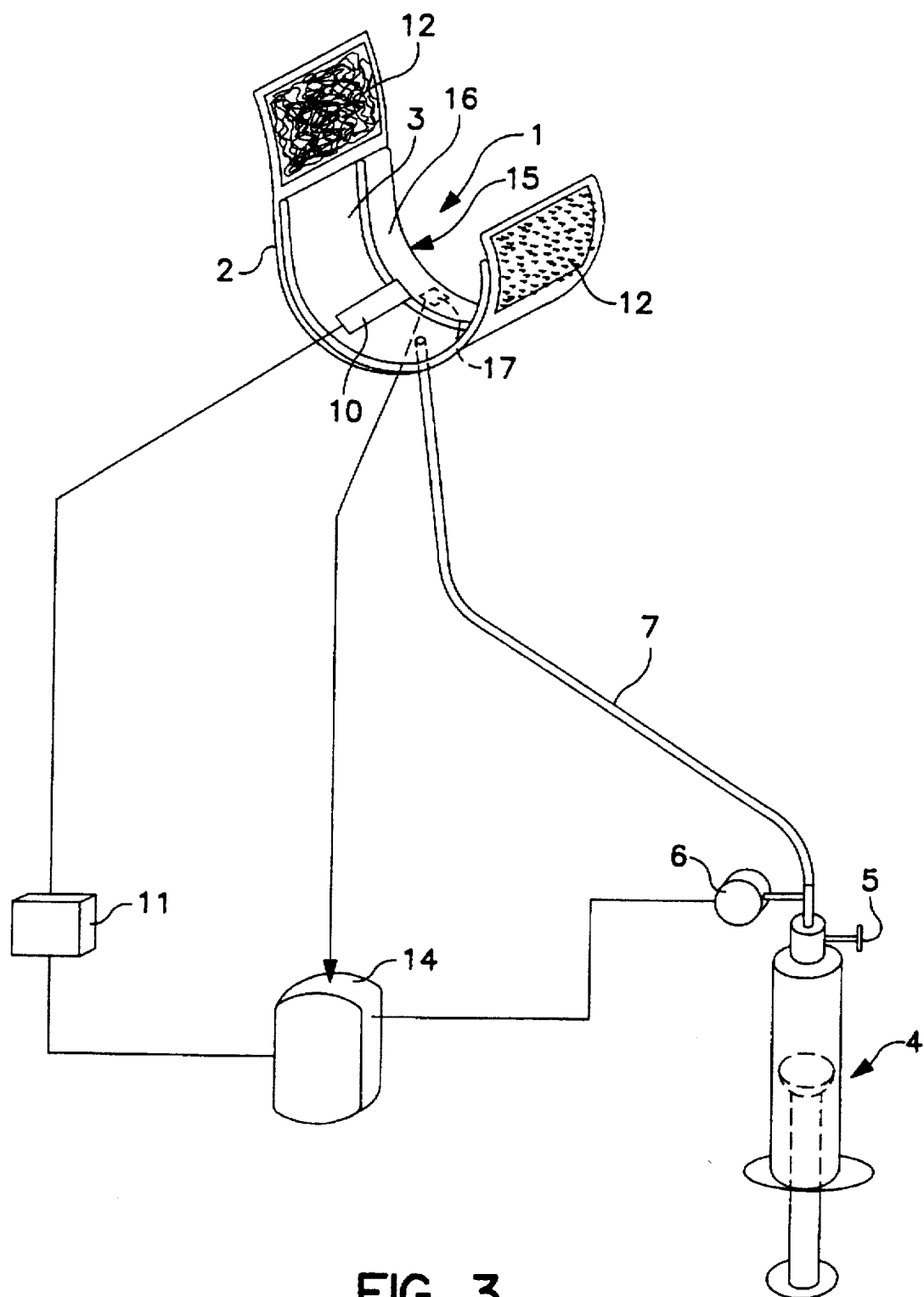
FIG. 3 is a schematic view of a third embodiment of the apparatus of the invention.

Additionally, the apparatus of this invention may be combined with a penile circumference measuring means, such as a mercury filled gauge 15 like the standard plethysmograph used to measure increases in penile circumference. This combination provides a means whereby the compliance of the corpus cavernosum may be calculated as the result of the change in Volume divided by the change in ICP. Thus, the ICP is measured using the pressure cuff of the invention simultaneously with the measurement of penile circumference from the mercury gauge. The change in Volume is derived from the change in penile circumference, and is then divided by the change in ICP as measured by the pressure cuff to obtain a value for the compliance of the corpus cavernosum. The mercury gauge, or plethysmograph, may be provided as a separate cuff which is applied to the penis adjacent to the cuff 1 of the present apparatus, or it may be incorporated into the cuff 1 as shown in FIG. 3. In this embodiment, the mercury filled gauge 15 is formed as a separate container 16 on the cuff 1. A signal generator 17 senses the variation in electrical resistance and provides a signal to the recording unit 14 or the computer 8 which is translated into a measure of the increase in penile circumference.

Although described primarily in connection with the measurement of tumescence and intra-cavernosal pressure of the penis for diagnosis in cases of erectile dysfunction, the apparatus of this invention is suitable for use in the measurement of blood flow and pressure in other appendages of the body, for example the hand or foot of stationary or ambulatory patients. Using the apparatus of this invention and the same or similar methods, one can measure, monitor and evaluate changes in arterial and venous blood flow and tissue pressures in other appendages over a period of time and particular activity.

The above embodiments and drawings illustrate the preferred embodiments of the present invention and it is understood that many variations and modifications of those embodiments will be evident to those skilled in the art and may be carried out without departing from the spirit and scope of the present invention.

What is claimed is:

1. A method for measuring penile rigidity comprising the steps of:

providing an apparatus for measuring arterial and venous blood flow and tissue pressure in body appendages, the apparatus comprising:

a cuff comprising a flexible, non elastic band, one face of which is covered with at least one plastic container capable of being filled with a fluid, means to position, close and firmly hold said band around a body appendage of the patient with said container on the inside of the cuff against said appendage, a pressure transducer in direct communication with the fluid inside said container to measure the pressure of said fluid, and electronic means to modify the sensitivity of the pressure transducer and to amplify and/or display signals generated by said transducer, the improvement comprising said cuff wherein said band has two longitudinally parallel containers covering one face of said band, wherein a first container is capable of being filled with a non compressible liquid and a second container is capable of being filled with a gas and said pressure transducer is in direct communication with the liquid in said first container wherein said pressure in said second container is maintained at a constant level, wrapping said cuff around the penis of a patient while said penis is non erect with said filled containers and said photoplethysmography probe in direct contact with said penis, closing said cuff to rigidly hold said filled containers and photoplethysmography probe against said penis, measuring the pressure of the fluid within said first container as said penis becomes erect, emitting, during said pressure measurement, a light beam from said photoplethysmography probe and measuring a reflected light beam with said probe, and amplifying, recording and displaying data from said measurements.

2. The method of claim 1 wherein said light beam emitted by said photoplethysmography probe is directed toward said penis.

3. The method of claim 1 further comprising the steps of:

recording a pulse signal with said photoplethysmography probe while said penis is non erect and during penile tumescence, for measured pressures inferior to a preset pressure value, recording a signal from said pressure transducer above said preset pressure value, and obtaining a curve of the pulse signal recording and the pressure transducer signal and evaluation of the pulse from a surface area under each curve, whereby a curve representative of changes in arterial blood flow during penile tumescence is obtained.

4. The method of claim 3 further comprising the steps of:

recording a signal from said pressure transducer for pressures inferior to said preset pressure value, obtaining a curve of said pressure signal, and applying fluid mechanics laws to calculate from said curve and said curve of changes in arterial blood flow, changes in venous blood flow, whereby a curve representative of changes in venous blood flow is obtained.

5. A method for measuring nocturnal penile tumescence and intra-cavernosal pressure while a patient is sleeping and diagnosing erectile dysfunction comprising the steps of:

providing an apparatus for measuring arterial and venous blood flow and tissue pressure in body appendages, the apparatus comprising:

a cuff comprising a flexible, non elastic band, one face of which is covered with at least one plastic container capable of being filled with a fluid, means to position, close and firmly hold said band around a body appendage of the patient with said container on the inside of the cuff against said appendage, a pressure transducer in direct communication with the fluid inside said container to measure the pressure of said fluid, and electronic means to modify the sensitivity of the pressure transducer and to amplify and/or display signals generated by said transducer, the improvement comprising said cuff wherein said band has two longitudinally parallel containers covering one face of said band, wherein a first container is capable of being filled with a non compressible liquid and a second container is capable of being filled with a gas and said pressure transducer is in direct communication with the liquid in said first container wherein said pressure in said second container is maintained at a constant level, wrapping said cuff around the penis of a patient while said penis is non erect with said filled containers and said photoplethysmography probe in direct contact with said penis, closing said cuff to rigidly hold said filled containers and photoplethysmography probe against said penis, measuring the pressure of the fluid within said first container as said penis becomes erect, emitting, during said pressure measurement, a light beam from said photoplethysmography probe and measuring a reflected light beam with said probe, amplifying, recording and displaying data from said measurements, obtaining and plotting curves from said data, for each tumescence period, identifying a period of pressure plateau corresponding to a vascular phase and identifying pressure peaks corresponding to muscular phases, evaluating surface areas of said plateau and of said peaks and transferring the results to an X-Y graph wherein the plateau surface area is plotted on the X-axis and the surface area of the peaks is plotted on the Y-axis, and plotting a curve with time on the X-axis and the plateau pressure and maximum peak pressures on the Y-axis, whereby said curve provides a means to analyze and classify a patient's erectile dysfunction.

6. In an apparatus for measuring arterial and venous blood flow and tissue pressure in body appendages, the apparatus comprising:

a cuff comprising a flexible, non elastic band, one face of which is covered with at least one plastic container capable of being filled with a fluid, means to position, close and firmly hold said band around a body appendage of the patient with said container on the inside of the cuff against said appendage, a pressure transducer in direct communication with the fluid inside said container to measure the pressure of said fluid, and electronic means to modify the sensitivity of the pressure transducer and to amplify and/or display signals generated by said transducer, the improvement comprising said cuff wherein said band has two longitudinally parallel containers covering one face of said band, wherein a first container is capable of being filled with a non compressible liquid and a second container is capable of being filled with a gas and said pressure transducer is in direct communication with the liquid in said first container.

7. The apparatus of claim 6 further comprising a photoplethysmograph in combination with said cuff wherein a probe of said photoplethysmograph is attached to said second container.

8. The apparatus of claim 7 wherein said probe of said photoplethysmograph is attached to said second container so that a light beam emitted by said probe is directed toward said appendage.

9. The apparatus of claim 7 wherein said second container is transparent.

10. The apparatus of claim 7 wherein pressure in said second container is maintained at a constant level.

11. The apparatus of claim 7 wherein said electronic means comprises a computer.

12. The apparatus of claim 7 wherein said electronic means comprises a portable recording unit capable of recording and subsequently downloading data corresponding to signals generated by said pressure transducer and said photoplethysmograph.

13. The apparatus of claim 6 wherein said electronic means comprises a computer.

14. The apparatus of claim 6 wherein said electronic means comprises a portable recording unit capable of recording, storing and subsequently downloading data corresponding to said signals.

15. The apparatus of claim 6 further comprising means to measure changes in penile circumference.

* * * * *